US005824309A

United States Patent [19]

DasSarma et al.

[11] Patent Number: 5,824,309
[45] Date of Patent: Oct. 20, 1998

[54] RECOMBINANT GAS VESICLES AND USES THEREOF

[75] Inventors: Shiladitya DasSarma; Fazeela Morshed; Elizabeth Stuart, all of Amherst; Samuel Black, Leverett, all of Mass.

[73] Assignee: University of Massachusetts, Boston, Mass.

[21] Appl. No.: 759,444

[22] Filed: Dec. 5, 1996

[51] Int. Cl.$^6$ .......................... A61K 39/21; A61K 39/02; A61K 39/295; C07K 14/195
[52] U.S. Cl. ...................... 424/188.1; 424/190.1; 424/201.1; 424/204.1; 424/207.1; 424/208.1; 424/234.1; 514/2; 530/350
[58] Field of Search ................... 435/69.1, 320.1, 435/172.1, 69.3, 172.3; 530/350; 514/2; 424/185.1, 234.1, 186.1, 187.1, 188.1, 190.1, 201.1, 204.1, 207.1, 208.1

[56] References Cited

PUBLICATIONS

Aldovini et al., "Synthesis of the complete trans–activation gene product of human T–lymphotropic virus type III in Escherichia Coli: . . . " Proc. Natl. Acad. Sci. USA 83:6672–6676, 1986.
J.S. Allan, "Major Glycoprotein Antigens Taht Induce Antibodies in AIDS Patients Are Encoded by HTLV–III" Science 228:1091–1094, 1985.
Muster et al., "A Conserved Neutralizing Epitope on gp41 of Human Immunodeficiency Virus Type 1" J. of Virology 67(11):6642–6647, 1993.
Blaseio et al., "Transformation of Halobacterium halobium: Development of vectors and investigation of gas vesicle synthesis" Proc. Natl., Acad. Sci. USA 87:6772–6776, 1990.
DasSarma et al., "Wild–Type Gas Vesicle Formation Requires at Least Ten Genes in the gvp Gene Cluster . . . " J. of Bacteriology 176(24):7646–7652, 1994.
DasSarma et al., "Gas Vesicle Proteins and Genes" Mol. Biol. 12:93–98, 1993.
Halladay et al., "The Rightward Gas Vesicle Operon in Halobacterium Plasmid pNRC100: . . . " J. of Bacteriology 175(3):684–692, 1993.
Halladay et al., Genetic transformation of a halophilic archaebacterium with a gas vesicle gene cluster restores.
Jones et al., "Structure and organization of the gas vesicle gene cluster on the Halobacterium Halobium plasmid pNRC100" Gene 102:117–122, 1991.

*Primary Examiner*—David Guzo
*Attorney, Agent, or Firm*—Fish & Richardson, P.C.

[57] ABSTRACT

The invention features a composition that includes a substantially pure recombinant gas vesicles which have at least one heterologous peptide inserted into at one of their structural proteins. The recombinant gas vesicle, when administered to a mammal, is capable of eliciting antibodies which specifically bind to the heterologous peptide. The heterologous peptide can be any peptide against which one wishes to raise antibodies, e.g., a peptide found in the gp12O protein of human immunodeficiency virus (HIV).

10 Claims, 12 Drawing Sheets

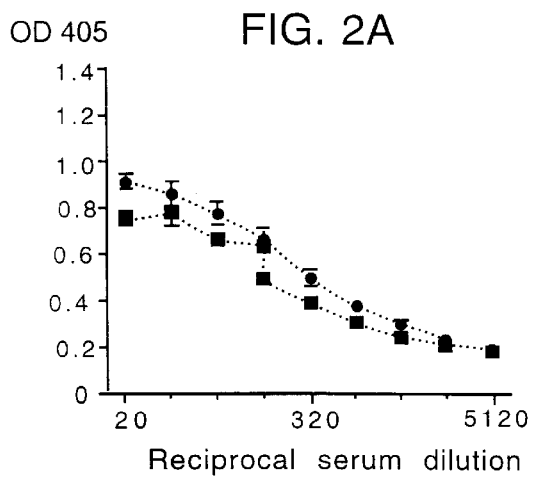
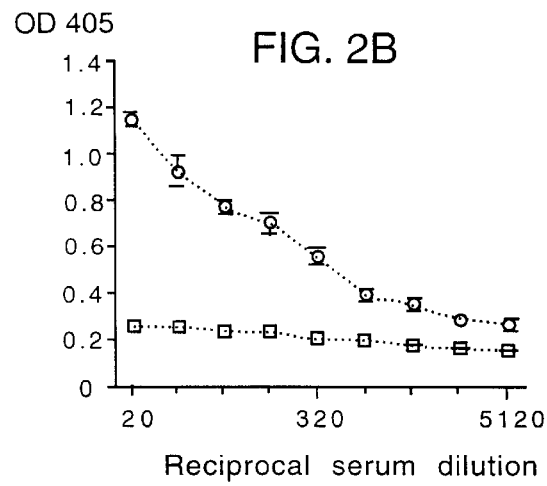
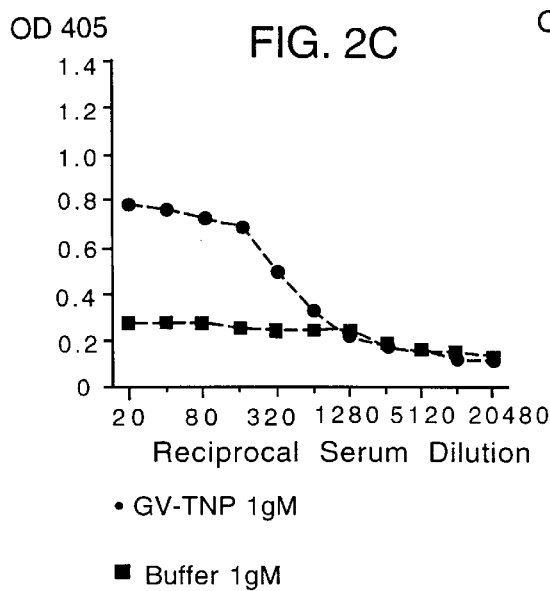
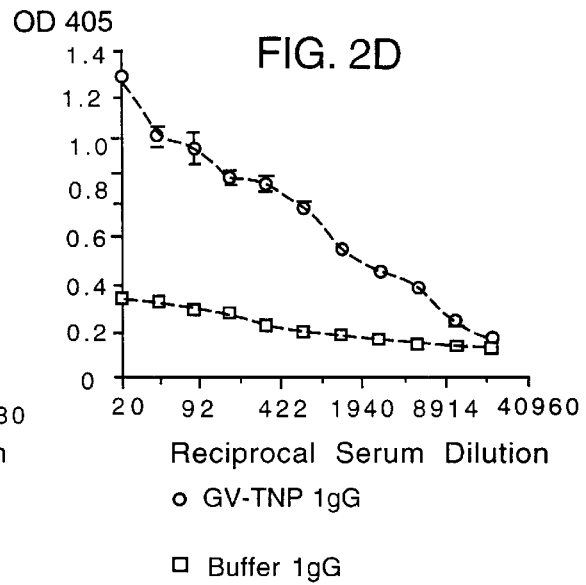

ISH8

| | | | | | | |
|---|---|---|---|---|---|---|
| GTGAGTCTTA | ACTGAAGACG | AATGCCGTGT | CGGGATTGAG | CGAGCAGAAA | CGCACCTCAC | 60 |
| GGACTCCGAA | GTCCAGGAGA | AGACCTCCTA | TGACGGGAAC | GTGGATCAGA | TCGAGACCTG | 120 |
| CATCGTTTAC | GATGGAATCG | ACGAGGAATA | CCTCGAGAAG | TGCCGGAACG | AATGGGACAA | 180 |
| CTGCCGGGAA | AAGCTAGAGA | AACTCGAAGA | ACAAACCGCC | ATCCTCACAC | AGGGACATGG | 240 |
| AGAGTCATTG | CGGTTGCTCA | CTGGAGAGTT | CGACTCTACT | CGACTACAAT | CCCGCTTCGA | 300 |
| GAGCGGTATC | GATCTCCCGG | TGAATCCGAA | GACAGAGTTC | GTCGCTGCCG | TCCCCGGCAG | 360 |
| TGGGCTCGTC | GAAAGACGCC | GAACCCGATC | CGGAACGACT | CCGATCAGCG | AGAACAGTGG | 420 |
| TCTTGCCCGT | CCTGTCACCG | AAAATTTCGC | TCACACCGCG | GGTTACAGCG | CCACTACGAC | 480 |
| ACCAACCGCG | AACACGCGGA | GGCGATGATC | GACGTCGATC | GGGAACTGGA | GCAGGATGAG | 540 |
| AGTACCAGCG | CCGGAACTGA | ATGGGTCGAG | TTCGTCGACC | AGATTGAGAC | GTTCTGTAAA | 600 |
| CTCTCGGATG | GATTCGACGA | GAGTGAGATC | ACCGTCACGC | ACGATTCAGC | TACCCACTGC | 660 |
| GTCCGTATCT | CCGGCGCACA | CGAGAATTCA | ATCGATACGA | GTCCCGTCTC | CGAGACGATC | 720 |
| GACGGCGACG | TGGAGTGGCG | TTCGTCTGGA | CGCTACCTTG | TCCTCTCGTT | CCCGCTGTGA | 780 |
| ACCGGTGGTC | TTTCGCCTCG | CCACCGCTGT | GATTCAACAT | ATCCCAGTTG | GGTTTCCGCA | 840 |
| TTATCCCTCT | CCTTTATTCT | CACGCGACAC | GACCTCGAAT | CAGTCCTCTC | GCCGATCGGC | 900 | gvpM* **

| | | | | | | |
|---|---|---|---|---|---|---|
| AGTGGGCGAG | GTCGTGAACG | CTTCGCTCTG | TTGTCGATGC | GCAGCATCCC | ACTCCTCGAA | 960 |
| CAGGCCGTAC | TCCGTCATGG | TGGTCATGCC | AGCAATCGCT | GCCCGGAGGC | TGATCCCGAT | 1020 |
| CAGGGGAATG | TCGGCGACCG | TCACGATCAC | GTCCGCTTGA | ATCACGGCTC | CGTCGCGCAG | 1080 |

<<<gvpM

| | | | | | | |
|---|---|---|---|---|---|---|
| TAACACGTCG | ACGAACTCAA | CGATCGCGTG | TGTCTCGTCT | TTTGTTGGCT | CCATTATTTA | 1140 | gvpL***

| | | | | | | |
|---|---|---|---|---|---|---|
| CCAATATCTG | GCGCGAACGT | GTACGGTGGC | CACGGCCCCG | TGAATCTGAT | CTCTACACCC | 1200 |
| TCGTGTTCGA | CGATCGTATC | CAATCGATCA | CCGAGAGCGG | TCTCGTCGTC | CTCGTCCGCG | 1260 |
| AGAACGGCGA | ACGCACGAT | CTGTTCTTTC | TCGATGGACG | AGTGTTCGTC | CTGTAGCGGC | 1320 |
| GTATTCGTGT | CCTGTTCGGT | CAGGTCGTTC | ACGACCGGGG | TAATGGCCTC | TTTCAGTTGA | 1380 |
| TCTGCTAGTT | CCGTCCGGCG | CTCTCGTTTC | AGCTCTTGGA | GTCGCTGATC | GGACTGTTTC | 1440 |

FIG. 6A

```
TCGAGGAGGA ACTTTTTCCC TGCGCCCGAT TGTTGCTGGC GCTGTCGTAG TTCTCGGAGC   1500
CGGTCGTCTC GGTCTGCGAT GGTCTCCTCG AACGGTGCGG AATCCCACAA CAGATTGATT   1560
CGATACTCCC ACACTCCCGC GAACGACGCT AATTCGTCGC GGAAGCCCTC GTAGTGGTCT   1620
TCTAACCACC GTTCGATACT CGCATCACCG CCCTCGAGGA CCGTGTCGAA TCGCATCGGC   1680
AGCGGCGTAC CGAACGCGTC GCTCGCCGCG TCGACGACCT GCTGGTGCGT GACCAGCCAT   1740
CGCTTCACCT GTTCGAGGTC TTCCGTCTCG TAGACCGTCT CACAGTCATG GACGACGGCG   1800
CCCACGCCAT CGGCCTCGAC GACGTAGACA GGGTTGTCGT CGACCCCGGT CGTGGACAGG   1860
GTCGCCGATT CCGACGACGT GGTATCGACC ACGCAGTATA GATAGCGGCC GTTGCTGACC   1920
                                                          <<<gvpL
GTCCGTTCCT CGTTCGCTGT GGTCTGCTCT TCTTCCGGGC TGGGCCGGTG GTCAGTCATA   1980
                                                          gvpK ***
CGTCATCACG CTGGGATTCC GGCGAGCCGT GACCTGACGG TGTCTCGTGC TCGGATAGCT   2040
GTTCGATGGC GTCGCGGATC ACGTGATCGA GGTCCTCCCT AAACTCGGAG ACCTCGGCGT   2100
TGATATCCTC TTGCTGTTTC AGTCGCTCGA GCTCGTCTTC GAGGGCCTGT AATTGTCGCC   2160
CCAATCGTTC GATTTCGTCC TCTGAGAGCG ACCCGGATTC CATCCGACGC ACCGCTTCTT   2220
GTTCGAGGGC CTCGACCAGC AATTCGACGA CAGTTACGAC CAGCGCCGTG AGCCCGCCTT   2280
                                                          <<<gvpK
GCAAATCGTC CGCGTCGTCG TCGAGTGCTA GTTCCATCTC ATTTGGTCTC CTCCGCTGAC   2340
                                    gvpJ ** *
GTGGATGCCG TCGGCGTCGA ATCGTCCGAC AGTGGGTTCG TCGACTCGGT CTCCGATTGG   2400
GTTTCCGACG CCGGGTCGGA CTGGTCCGGT GAGATATTCG CGGCGGACTC GACGCGCTCC   2460
ATATCCGTCC CCGTTGGGAA CTCGAGCCCG TATTCGGCCG CTGTCTCGAA CGAAGCAATC   2520
GCGGCCCGTA ACTCGATACC GAGGAGTTCC GTGTCCCCGA CGCTGACTGC GATATCCGCG   2580
TTGACGACGA CTCCTTTGTC TAGGAGCATC TCCAGCATCT CGGCGAGGTC GCCCTGCGAG   2640
                    <<<gvpJ
CGCGTCGGTT TGGGGTCACT CATCGTTCAC CTCGTCCTCA GTGGGACTCC CGGACGCGCT   2700
            gvpI***
CTCATCCGAC GGGGCGGATG CCTCCGAGTT TCCACCGGCT GTTTTCTGGT GAAGCCGTTG   2760
GCCGTACAAT CGCTCTCGAG CCGTCACATC CGAGTACTTC GGAGTCTTCG GGACGGTCGA   2820
GTGGGAGTTG CGTACCGCGT TCTCCGCGTT CGACTTCTGA GGCGGCATCG TCGAGTGAGC   2880
CGCTGGATTC TTGACCGTCT CCCCGTCAGT ATCGTCGCCG TCGGAATCGT CACGCCGGGG   2940
TTCCGACTGT TTCCGGTTGC GGGTCCGACG CCGGGCGAGT TTTTCGCGCT GCCGAAGCAG   3000
ATTGCGCCGG GCTTTATCGC GGTTGATCTG CGCCTTTACT CGTGCCTGTC GTGCTTTCTG   3060
```

FIG. 6B

```
                            <<<gvpI
CTTGTGTTTT  TGCTGTTGTT  TGTCGCTCAT  GTGGATTCAC  CTCCATCGGT  GTCCGATGTT    3120
                        gvpH ***
CGTGCTAGCC  GAATTTCGAG  AACCTGATTT  CTGAGAGTCA  TATCGGTGAT  CGCCACGTCC    3180
GGCCGGTCGA  GTACGACTCG  CTCGACCACG  TCGTCGTCGA  CGCGTAGCGT  GAGTGCCTGC    3240
TCGTCGGTAT  CGAGTGCGAC  GTCGACGTCG  TCGTCCGTCA  CGCCCGGCAA  ATCTGCGACC    3300
ACGACGAGTT  CGTCGCCGCT  CGTTCCTCCA  CGAGTCTCGA  CGTGAATCGA  ATCCTCCGTC    3360
GTCCTTTGCT  GACCGGATCG  CTGTTCGGAG  CGGGACCGAT  TGGACGATGG  TTCCTCGTCG    3420
TAGGACGACC  CGTCCGCTCG  TCCCAGCCCG  ATGGAAACGT  CGTAGTCGTA  ATCAATTCGG    3480
GCGTTTCCCC  GGTCGATACG  GCCTGACTCG  TGTCGGTGAC  CGCCCTCCTC  TTCGATGTCG    3540
GCGAGCACCT  CGACGAGCGT  GTGCAATTGG  TCGAGCAGCC  CGCTGAGCTG  GAAGACTGG     3600
                                                <<<gvpH
TCGTCGGACG  CGTCGTCGTT  TTCGTCGGGT  ACCATTATTT  CTTGACCTCC  ATGCGGTCAC    3660
                                   gvpG ***
GCATCTGTTC  TTGGACCTGC  TCGGCCATCT  CCAGTTGCGA  TTCGAGTGCT  TGCTTGCGCT    3720
GCTGGTACTC  CTCGTCGGAT  CGTTCACCAA  CTTCGTACAG  GAGTTGGTTC  TCCTTGATGT    3780
CGTCTCGAAT  CGATTTGGTG  TCGTACATCT  CGTCGAGAGC  CATCGTCTGG  AGGATATCCA    3840
                                                <<<gvpG
GCAAGGAGAA  AAACGGGCTC  ACGAAGAGAT  CGTCTATGAT  GAACATGCAT  TATCGGCCTC    3900
                                                gvpF * **
CTTGTTGCTG  TTCCGCGCCG  ATGTGAATGT  CCACGAAATT  GTACGGCGGC  CACGGCCCCG    3960
TGTACTGAAT  CGTCAGTTCG  TCGTATTCCG  CTTCGACATC  GTCGATGGCG  GAGTCGAAAG    4020
CATCGCGTTT  CTCGAAGTCG  ACGAGGTACG  ACTTATTGAT  GATCAGGCGG  TCTGTGAAGA    4080
GATCGTTCTC  GGTCTCGTTG  ATACTCAGAT  CTGCTAGTTG  ATCCGTGACG  TTTTCCTGGA    4140
TTTCTTCTCG  AGGGACTGTA  TCGTCGCCAG  GACCGAGTAT  CTTCACGCCA  AGTTCGACGG    4200
TTCCCTCGAT  GTCATTCAGC  GTACTGCGCA  ATGCACGTCG  CGCCCCGCGC  AATACACCCT    4260
TTAGCGTGCG  CGCACTTTTG  AACGCCATCC  CGAAGCTCAT  CGGGACGACT  GTGCGTTCTT    4320
CTTCGTGCTT  CAATACCTCC  TGGAGCACGT  TGTTATGAGC  TTCCACGTCC  TCATCGGTGC    4380
GCTCGGGGTC  GGTCGTATCA  ATGTCAGAGA  CGACAGCGGA  GAGTGTCTTG  TAATCGACCG    4440
TATAGACCTG  TTCCGCTCCG  GCAACGCCTT  CGACATCTAA  TTCGAGATCT  TCCTGTTCGA    4500
                                   <<<gvpF
TGATACCGTA  TGTGTATAGG  TTCTCAGTCA  TTGGTCTCTC  TTCCTTGGGA  TTGTGATTGA    4560
                        gvpE ***
CGCGCCTTGC  AATCGGTCAT  AACCGCCTTG  AGTACGAGCG  AAAACAGCAG  CAACTGATCA    4620
ACCATGTGGT  CTATTCGGGT  GAACGCTCCT  TCAGGATCGG  AGAGGCGATA  CACTTTGCGC    4680
```

FIG. 6C

|  |  |  |  |  |  |
|---|---|---|---|---|---|
| TTGCTCAATT | TCTGTACCTC | AAGTACACCT | TCGACTGCAA | GGTCATTTAA | ATGCGGGTAT | 4740 |
| ACTGTACCCG | GACTCAGGTC | TGCCCCAAAC | AGCCGCCGGA | GATCCTGGAG | CAGTTCTTTT | 4800 |
| CCACAGGCAC | CGTCTCGCAC | AGTAATCAGA | AGAAGGAGAA | TCTCGTCGAT | ATGTTCGGTG | 4860 |
| ACGATGGCAT | CACTGATCGT | GTGAAGCTGG | TCATTATCAA | GCCACCCGTC | CATCGTAGCG | 4920 |
| ACCGCGTCAT | CAGTCAGCGG | CGTGTCCGTG | TAGCGTTGCG | TTGCCCCCTC | ATCAGGCGGC | 4980 |
| TGGTCTGCGT | GATCTGACGC | ACCGTCGGAT | TCGATCACTG | ATTCGAGATC | TGTGACTGCG | 5040 |
| AACGAGATCG | CGGCGTTAGC | ATCGATGTCT | GCGGTGAGTT | CCTCCAGCAA | GTCGTCCATT | 5100 |

<<<gvpE gvpD***

|  |  |  |  |  |  |
|---|---|---|---|---|---|
| GTTAGACCAT | CTCCGTGAGC | GTGATTTTGG | GGATCGACTC | TGACTGGCTG | ATGCCGATTC | 5160 |
| CGAGCAGGGG | CGTCAACGGG | TTTTCGCCAT | ACAGGATGAT | GGCGTCACCG | GACCGTTCCA | 5220 |
| GCCGGAAGTG | CATATCGGCA | ACCCGATCCG | CTCGCGTGCG | GAGTTCAGTA | CCTTGCTTGG | 5280 |
| TGATGAGCAG | TGTCAGGTCG | TTGTGGAGAG | CGACGTAATT | TGCAAAGTCA | CCTAGCCGGG | 5340 |
| TCTCAAATGC | CTCCTGCGCC | GTGTCCATGC | TGATCACGTG | CAACAACGGA | TCTTCACTTT | 5400 |
| CTTCTCGCAC | CTGTTCAACG | TAGGCCATGT | ATGGCTCGTA | CGCGAGTTGC | CCGCCCTCTA | 5460 |
| TCGGTGACTC | AAAGTCCTCA | TCAATCGGAT | GCGGCTGGTC | ACTCCCCGTA | ACTCCATCCG | 5520 |
| TCGAACGTGA | GCCATCGTCC | GCACCATCAG | TCTCATGCGT | CGCCGTCGGT | GCATCGTCCG | 5580 |
| GCGGCGTTGT | CGTTGCCATC | TCAGAAAATG | ACTCAGTGCT | GTCCGGTTGG | TCGTACCGAT | 5640 |
| CCGCACTGTC | AGAGGGGCCG | GCGTATGTTT | CGAAGACGTG | GCAGTAGGTA | TCGAAGACCT | 5700 |
| GTGAGGAGAG | CACAGTATTG | AGATCGTTGT | GGAGTAAGCC | AGGGCTGCCC | TCCCGGGGCG | 5760 |
| GGACAACCGC | AACCCCCATC | TCCTGAGAGA | GGAAGTTGCG | AATCGTCGGG | AGCGTCAACA | 5820 |
| CGCTCCACGC | GTCACGAGAC | AGATCGGGCC | CGAGGTCGAG | ATGAACGACG | CTGCCGCGGT | 5880 |
| TGTAGCCACC | CGAGAGGATA | CGGTCAAGAT | CACGGATGCC | AGTCGAGAAT | TCGCCTTCG | 5940 |
| AATTTGCCAG | GGGATCCCAC | GTGCCATTCC | CGGTTCCTGT | TTGGATGGTT | AGTAATTCGA | 6000 |
| CCGGCGTGAT | CACCTGGAAC | TGGCCGTCGG | CAAGCGTAAA | GGGCTGTAAG | CGGTTGCCGA | 6060 |
| TTCGAACGCC | CCGAAGCTTA | TCCAAGCGGA | GATCCCGACG | CGTTCGGCCA | CGGTCATCCT | 6120 |
| CCTTAACCTG | GAGGGTGACG | ACCCCATCGA | CGATGTATTC | AAGCGATGAG | GGCGCCGCTG | 6180 |
| TTTCTGTCAC | TAACATCAGA | CGAATGTTCT | CTTCGCGGGC | AAGAACGGCC | AGTTGATTCG | 6240 |
| TCACAGTCTT | GATGTCAGGG | GGGTCATCGT | GGCGAACAGC | CAAATACTCG | TAGATGAGTT | 6300 |

FIG. 6D

```
CCCAGCTATC GAATGCGATT GTGAGTTGCG TGGTCGCGGC GTTGATCTCT TGGATCCATT    6360
CGAGGAGCGA ATCCAGATCG AGTTTCTCGA ATGGCACGTC TACGTCCAGT GGGAGTTCGA    6420
ATGGGTCTTG GAAGAGGTCA AGAATCGCGG TTGTGTCGAG TGAGGAGTGA TCGGCGAAGT    6480
ACATCTCGTG AACCGTCTCC TGATCAACAC GTGTGGACAC GTAGAGGACA TCACTGTCTC    6540
GGTCCAACAC ATCGAGGCCG CGGATCGTGA ACAAGGTCTT ACCCGTGCCT GGTGCACCGT    6600
TAATGAGGAG CGTTTCCCCG GCGTCACCCA TGAAAAACTG GCTGAGCTCG CGGGGGAATA    6660
                                                     <<<gvpD
ACACGATTCC GGTGTAGTCT GTGGGCGGGT GAGCTAGATT GGGTGAACTC ATTACTTCTC    6720
TCCAGTCGAT GGCGGTAGAG CACTCCCGAC TAGTAGGTGA GGCTTTCTTC GCTTCACGAC    6780
◄┐PD
TGTCTAAGAA GCTTTACACT CTCCGTACTT AGAAGTACGA CTCATTACAG GAGACATAAC    6840
                                                          PA┌─►
GACTGGTGAA ACCATACACA TCCTTATGTG ATGCCCGAGT ATAGTTAGAG ATGGGTTAAT    6900
              gvpA>>>
CCCAGATCAC CAATGGCGCA ACCAGATTCT TCAGGCTTGG CAGAAGTCCT TGATCGTGTA    6960
CTAGACAAAG GTGTCGTTGT GGACGTGTGG GCTCGTGTGT CGCTTGTCGG CATCGAAATC    7020
CTGACCGTCG AGGCGCGGGT CGTCGCCGCC TCGGTGGACA CCTTCCTCCA CTACGCAGAA    7080
GAAATCGCCA AGATCGAACA AGCCGAACTT ACCGCCGGCG CCGAGGCGGC ACCCGAGGCC    7140
TGACGCACAG GCCTCCCTTC GGCCGGCGTA AGGGAGGTGA ATCGCTTGCA AACCATACTA    7200
***gvpA                              gvpC>>>
TTAACACCTT CTCGGGTACA CACTAATCCC ATGAGTGTCA CAGACAAACG CGACGAGATG    7260
AGTACTGCCC GCGATAAGTT CGCAGAATCA CAGCAGGAGT TCGAATCATA CGCTGACGAG    7320
TTTGCAGCCG ATATCACGGC AAAGCAAGAC GATGTCAGCG ACCTTGTCGA TGCGATCACC    7380
GACTTCCAGG CGGAGATGAC CAACACGACG GATGCATTTC ACACATATGG TGACGAGTTC    7440
GCCGCTGAGG TTGACCACCT CCGTGCCGAT ATTGACGCCC AGCGGGACGT GATCCGTGAG    7500
ATGCAGGATG CGTTCGAGGC ATATGCTGAC ATCTTCGCTA CAGATATCGC AGACAAACAA    7560
GATATCGGCA ATCTTCTGGC TGCGATTGAG GCGCTCCGAA CAGAGATGAA CTCAACCCAC    7620
GGGGCATTCG AAGCATATGC GGACGACTTC GCAGCCGATG TCGCTGCGCT CCGTGATATA    7680
TCTGATCTGG TTGCAGCAAT CGACGACTTC CAAGAGGAAT TCATCGCCGT GCAGGACGCA    7740
TTTGACAACT ACGCTGGTGA CTTCGATGCG GAGATCGACC AGCTCCACGC TGCCATCGCT    7800
GACCAGCACG ACAGCTTCGA CGCTACCGCG GACGCCTTCG CAGAGTACCG AGATGAGTTC    7860
TATCGCATAG AGGTGGAAGC ACTGCTTGAG GCGATCAACG ACTTCCAGCA GGACATCGGT    7920
```

FIG. 6E

```
GACTTCCGAG CGGAGTTTGA AACGACTGAG GACGCGTTCG TTGCCTTCGC CCGTGACTTC    7980
TATGGCCACG AGATCACGGC CGAGGAAGGC GCCGCCGAAG CGGAAGCCGA ACCCGTCGAG    8040
GCTGACGCGG ACGTCGAAGC GGAAGCAGAA GTCTCTCCAG ACGAAGCTGG CGGAGAATCC    8100
GCCGGTACCG AGGAAGAAGA GACAGAGCCG GCCGAGGTGG AAACAGCGGC TCCAGAAGTA    8160
GAGGGGAGTC CTGCGGACAC GGCAGACGAA GCGGAAGATA CGGAAGCAGA GGAGGAGACA    8220
GAGGAAGAGG CACCGGAAGA CATGGTGCAG TGCCGGGTGT GCGGCGAATA CTATCAGGCC    8280
ATCACGGAGC CCCATCTCCA GACCCATGAT ATGACGATTC AGGAGTACCG CGACGAGTAC    8340
                                           gvpN>>>
GGTGAGGATG TCCCCCTTCG GCCGGATGAT AAAACATGAC GAACGAGTCC CGTAAACGCA    8400
                                 *** gvpC
AGGTACGAGG GTCGCAGATC CGCTCCTCAC GCGGCGACAA GAAACAGGGG CGATCACAGA    8460
GCCGTGATGA TAAGGAGATC GAGCGTCTCG AGAGGCAGAA CGACGCTCGT GGCCAGGAGT    8520
CGTCTACCCA CGTCGACGAG GGGTTCGTTC CGAGGAACA GTCCTTCATC GAGACCGAAT    8580
CGGTCAATCG AGTCGAGTCG CGGATGGAAC GGTGGCTCGA TGTCGGACGT CCGGTTCACC    8640
TGATCGGGCC GACCGGCTGT GGGAAAACGT CGCTGGCGAT GCACGTCGCG CGCGAGCGCG    8700
ATCGCCCGGT CGTCTGGATC AACGGCGACG CCGAACTCAC GACCAGCGAT CTCGTCGGCG    8760
AATACGCGGA AAAAGAGCGC ATCTCGGAGC ACGATCAATT CATCCACAAC GTCGTTAAGA    8820
GCAAGGACAT CATCCGTGAT CGATGGGTGG ACAACCCCCT GACGCTCGCC GTACAAGAGG    8880
GGGCAACGCT GGTCTACAAC GAGTTCTCCC GCACCAAGCC CGTCGCAAAC AACGTGCTGT    8940
TGTCGGTCTT CGAGGAAGGG GTGCTCGAAC TGCCGGGGAA ACGCGGCAAA TCTCGGTATG    9000
TAGATGTGCA TCCTGAGTTC CGAACCATCC TGACCTCGAA CTCCGTCGAG TACGCTGGCG    9060
TCCACGAGCC GCAAGACGCC CTGCTCGACC GCCTCATCGG GATCTACATG GATTTCTACG    9120
ATCTCGACAC GGAGATCGAG ATCGTTCGGG CGCACGTCGA CAAGTCGGCC GACACAAACG    9180
TCGAGGACAT CGTGCGGGTT CTGCGTGAAC TCCGCGAGCG GCTCGATATC ACCGTGGGTA    9240
CACGGGCCGC GATTATGGCC AACGAAGGCG CTACCACCGT CGACACCGTC GACCAGGCCG    9300
TCCTGACCGA TATCTGTACC GACGTGCTGG CATCGAAGGT CGCCCAGCGG AGCGACGTTC    9360
GCGGGCTGCG CGAAGAAATA GAATCCGCGA TCGACGACAT GGAAGTCGCC CTTTCTTAAG    9420
                                                        *** gvpN
ATCCGGGGTC TCTACATAGA AGCATGGCAG ATCCAGCAAA CGATCGATCT GAACGCGAGG    9480
AAGGCGGCGA GGACGACGAA ACACCGCCAG CGTCCGACGG GAACCCCTCG CCGTCGGCCA    9540
```

FIG. 6F

```
ATTCATTCAC TCTCTCCAAC GCGCAGACGC GCGCACGAGA GGCGGCACAG GACCTGTTGG    9600
AACACCAGTT CGAGGGATTG ATCAAAGCCG AGTCGAACGA CGAAGGCTGG CGGACCGTCG    9660
TCGAAGTCGT CGAACGGAAC GCCGTACCCG ATACACAAGA CATCATCGGT CGCTACGAGA    9720
TCACGCCTTG ACGGGACGGG GGACGTCACC GGCTACGAGC TCCTAGAACG CTATCGTCGG    9780
GGCGACATGA AAGAGGAACT GTAGCGGTGC GTCAAATGCA CGAGCAATAG ATATGGCCCA    9840
TCGACTGACC GTAGCGAACG AGAAAGGCGG CGTGGGGAAG                          9880
```

FIG. 6G

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: linear (ii) MOLECULE TYPE: peptide (xi) SEQUENCE DESCRIPTION: SEQ ID NO:1:

```
Glu  Ser  Ser  Gly  Thr  Phe  Glu
 1              5
```

(2) INFORMATION FOR SEQ ID NO:2:

(i) SEQUENCE CHARACTERISTICS:
        (A) LENGTH: 8878 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

```
GCCCGGAGGC  TGATCCCGAT  CAGGGGAATG  TCGGCGACCG  TCACGATCAC  GTCCGCTTGA    60
ATCACGGCTC  CGTCGCGCAG  TAACACGTCG  ACGAACTCAA  CGATCGCGTG  TGTCTCGTCT   120
TTTGTTGGCT  CCATTATTTA  CCAATATCTG  GCGCGAACGT  GTACGGTGGC  CACGGCCCCG   180
TGAATCTGAT  CTCTACACCC  TCGTGTTCGA  CGATCGTATC  CAATCGATCA  CCGAGAGCGG   240
TCTCGTCGTC  CTCGTCCGCG  AGAACGGCGA  ACCGCACGAT  CTGTTCTTTC  TCGATGGACG   300
AGTGTTCGTC  CTGTAGCGGC  GTATTCGTGT  CCTGTTCGGT  CAGGTCGTTC  ACGACGGGG    360
TAATGGCCTC  TTTCAGTTGA  TCTGCTAGTT  CCGTCCGGCG  CTCTCGTTTC  AGCTCTTGGA   420
GTCGCTGATC  GGACTGTTTC  TCGAGGAGGA  ACTTTTTCCC  TGCGCCCGAT  TGTTGCTGGC   480
GCTGTCGTAG  TTCTCGGAGC  CGGTCGTCTC  GGTCTGCGAT  GGTCTCCTCG  AACGGTGCGG   540
AATCCCACAA  CAGATTGATT  CGATACTCCC  ACACTCCCGC  GAACGACGCT  AATTCGTCGC   600
GGAAGCCCTC  GTAGTGGTCT  TCTAACCACC  GTTCGATACT  CGCATCACCG  CCCTCGAGGA   660
CCGTGTCGAA  TCGCATCGGC  AGCGGCGTAC  CGAACGCGTC  GCTCGCCGCG  TCGACGACCT   720
GCTGGTGCGT  GACCAGCCAT  CGCTTCACCT  GTTCGAGGTC  TTCCGTCTCG  TAGACCGTCT   780
CACAGTCATG  GACGACGGCG  CCCACGCCAT  CGGCCTCGAC  GACGTAGACA  GGGTTGTCGT   840
CGACCCCGGT  CGTGGACAGG  GTCGCCGATT  CCGACGACGT  GGTATCGACC  ACGCAGTATA   900
GATAGCGGCC  GTTGCTGACC  GTCCGTTCCT  CGTTCGCTGT  GGTCTGCTCT  TCTTCCGGGC   960
TGGGCCGGTG  GTCAGTCATA  CGTCATCACG  CTGGGATTCC  GGCGAGCCGT  GACCTGACGG  1020
TGTCTCGTGC  TCGGATAGCT  GTTCGATGGC  GTCGCGGATC  ACGTGATCGA  GGTCCTCCCT  1080
AAACTCGGAG  ACCTCGGCGT  TGATATCCTC  TTGCTGTTTC  AGTCGCTCGA  GCTCGTCTTC  1140
GAGGGCCTGT  AATTGTCGCC  CCAATCGTTC  GATTTCGTCC  TCTGAGAGCG  ACCCGGATTC  1200
CATCCGACGC  ACCGCTTCTT  GTTCGAGGGC  CTCGACCAGC  AATTCGACGA  CAGTTACGAC  1260
CAGCGCCGTG  AGCCCGCCTT  GCAAATCGTC  CGCGTCGTCG  TCGAGTGCTA  GTTCCATCTC  1320
ATTTGGTCTC  CTCCGCTGAC  GTGGATGCCG  TCGGCGTCGA  ATCGTCCGAC  AGTGGGTTCG  1380
TCGACTCGGT  CTCCGATTGG  GTTTCCGACG  CCGGGTCGGA  CTGGTCCGGT  GAGATATTCG  1440
CGGCGGACTC  GACGCGCTCC  ATATCCGTCC  CCGTTGGGAA  CTCGAGCCCG  TATTCGGCCG  1500
CTGTCTCGAA  CGAAGCAATC  GCGGCCCGTA  ACTCGATACC  GAGGAGTTCC  GTGTCCCCGA  1560
CGCTGACTGC  GATATCCGCG  TTGACGACGA  CTCCTTTGTC  TAGGAGCATC  TCCAGCATCT  1620
CGGCGAGGTC  GCCCTGCGAG  CGCGTCGGTT  TGGGGTCACT  CATCGTTCAC  CTCGTCCTCA  1680
GTGGGACTCC  CGGACGCGCT  CTCATCCGAC  GGGGCGGATG  CCTCCGAGTT  TCCACCGGCT  1740
GTTTTCTGGT  GAAGCCGTTG  GCCGTACAAT  CGCTCTCGAG  CCGTCACATC  CGAGTACTTC  1800
```

```
GGAGTCTTCG  GGACGGTCGA  GTGGGAGTTG  CGTACCGCGT  TCTCCGCGTT  CGACTTCTGA   1860
GGCGGCATCG  TCGAGTGAGC  CGCTGGATTC  TTGACCGTCT  CCCCGTCAGT  ATCGTCGCCG   1920
TCGGAATCGT  CACGCCGGGG  TTCCGACTGT  TTCCGGTTGC  GGGTCCGACG  CCGGGCGAGT   1980
TTTTCGCGCT  GCCGAAGCAG  ATTGCGCCGG  GCTTTATCGC  GGTTGATCTG  CGCCTTTACT   2040
CGTGCCTGTC  GTGCTTTCTG  CTTGTGTTTT  TGCTGTTGTT  TGTCGCTCAT  GTGGATTCAC   2100
CTCCATCGGT  GTCCGATGTT  CGTGCTAGCC  GAATTCGAG   AACCTGATTT  CTGAGAGTCA   2160
TATCGGTGAT  CGCCACGTCC  GGCCGGTCGA  GTACGACTCG  CTCGACCACG  TCGTCGTCGA   2220
CGCGTAGCGT  GAGTGCCTGC  TCGTCGGTAT  CGAGTGCGAC  GTCGACGTCG  TCGTCCGTCA   2280
CGCCCGGCAA  ATCTGCGACC  ACGACGAGTT  CGTCGCCGCT  CGTTCCTCCA  CGAGTCTCGA   2340
CGTGAATCGA  ATCCTCCGTC  GTCCTTTGCT  GACCGGATCG  CTGTTCGGAG  CGGGACCGAT   2400
TGGACGATGG  TTCCTCGTCG  TAGGACGACC  CGTCCGCTCG  TCCCAGCCCG  ATGGAAACGT   2460
CGTAGTCGTA  ATCAATTCGG  GCGTTTCCCC  GGTCGATACG  GCCTGACTCG  TGTCGGTGAC   2520
CGCCCTCCTC  TTCGATGTCG  GCGAGCACCT  CGACGAGCGT  GTGCAATTGG  TCGAGCAGCC   2580
CGCTGAGCTG  GGAAGACTGG  TCGTCGGACG  CGTCGTCGTT  TTCGTCGGGT  ACCATTATTT   2640
CTTGACCTCC  ATGCGGTCAC  GCATCTGTTC  TTGGACCTGC  TCGGCCATCT  CCAGTTGCGA   2700
TTCGAGTGCT  TGCTTGCGCT  GCTGGTACTC  CTCGTCGGAT  CGTTCACCAA  CTTCGTACAG   2760
GAGTTGGTTC  TCCTTGATGT  CGTCTCGAAT  CGATTTGGTG  TCGTACATCT  CGTCGAGAGC   2820
CATCGTCTGG  AGGATATCCA  GCAAGGAGAA  AAACGGGCTC  ACGAAGAGAT  CGTCTATGAT   2880
GAACATGCAT  TATCGGCCTC  CTTGTTGCTG  TTCCGCGCCG  ATGTGAATGT  CCACGAAATT   2940
GTACGGCGGC  CACGGCCCCG  TGTACTGAAT  CGTCAGTTCG  TCGTATTCCG  CTTCGACATC   3000
GTCGATGGCG  GAGTCGAAAG  CATCGCGTTT  CTCGAAGTCG  ACGAGGTACG  ACTTATTGAT   3060
GATCAGGCGG  TCTGTGAAGA  GATCGTTCTC  GGTCTCGTTG  ATACTCAGAT  CTGCTAGTTG   3120
ATCCGTGACG  TTTTCCTGGA  TTTCTTCTCG  AGGGACTGTA  TCGTCGCCAG  GACCGAGTAT   3180
CTTCACGCCA  AGTTCGACGG  TTCCCTCGAT  GTCATTCAGC  GTACTGCGCA  ATGCACGTCG   3240
CGCCCCGCGC  AATACACCCT  TTAGCGTGCG  CGCACTTTTG  AACGCCATCC  CGAAGCTCAT   3300
CGGGACGACT  GTGCGTTCTT  CTTCGTGCTT  CAATACCTCC  TGGAGCACGT  TGTTATGAGC   3360
TTCCACGTCC  TCATCGGTGC  GCTCGGGGTC  GGTCGTATCA  ATGTCAGAGA  CGACAGCGGA   3420
GAGTGTCTTG  TAATCGACCG  TATAGACCTG  TTCCGCTCCG  GCAACGCCTT  CGACATCTAA   3480
TTCGAGATCT  TCCTGTTCGA  TGATACCGTA  TGTGTATAGG  TTCTCAGTCA  TTGGTCTCTC   3540
TTCCTTGGGA  TTGTGATTGA  CGCGCCTTGC  AATCGGTCAT  AACCGCCTTG  AGTACGAGCG   3600
AAAACAGCAG  CAACTGATCA  ACCATGTGGT  CTATTCGGGT  GAACGCTCCT  TCAGGATCGG   3660
AGAGGCGATA  CACTTTGCGC  TTGCTCAATT  TCTGTACCTC  AAGTACACCT  TCGACTGCAA   3720
GGTCATTTAA  ATGCGGGTAT  ACTGTACCCG  GACTCAGGTC  TGCCCCAAAC  AGCCGCCGGA   3780
GATCCTGGAG  CAGTTCTTTT  CCACAGGCAC  CGTCTCGCAC  AGTAATCAGA  AGAAGGAGAA   3840
TCTCGTCGAT  ATGTTCGGTG  ACGATGGCAT  CACTGATCGT  GTGAAGCTGG  TCATTATCAA   3900
GCCACCCGTC  CATCGTAGCG  ACCGCGTCAT  CAGTCAGCGG  CGTGTCCGTG  TAGCGTTGCG   3960
TTGCCCCCTC  ATCAGGCGGC  TGGTCTGCGT  GATCTGACGC  ACCGTCGGAT  TCGATCACTG   4020
ATTCGAGATC  TGTGACTGCG  AACGAGATCG  CGGCGTTAGC  ATCGATGTCT  GCGGTGAGTT   4080
CCTCCAGCAA  GTCGTCCATT  GTTAGACCAT  CTCCGTGAGC  GTGATTTTGG  GGATCGACTC   4140
TGACTGGCTG  ATGCCGATTC  CGAGCAGGGG  CGTCAACGGG  TTTTCGCCAT  ACAGGATGAT   4200
```

-continued

```
GGCGTCACCG   GACCGTTCCA   GCCGGAAGTG   CATATCGGCA   ACCCGATCCG   CTCGCGTGCG   4260
GAGTTCAGTA   CCTTGCTTGG   TGATGAGCAG   TGTCAGGTCG   TTGTGGAGAG   CGACGTAATT   4320
TGCAAAGTCA   CCTAGCCGGG   TCTCAAATGC   CTCCTGCGCC   GTGTCCATGC   TGATCACGTG   4380
CAACAACGGA   TCTTCACTTT   CTTCTCGCAC   CTGTTCAACG   TAGGCCATGT   ATGGCTCGTA   4440
CGCGAGTTGC   CCGCCCTCTA   TCGGTGACTC   AAAGTCCTCA   TCAATCGGAT   GCGGCTGGTC   4500
ACTCCCCGTA   ACTCCATCCG   TCGAACGTGA   GCCATCGTCC   GCACCATCAG   TCTCATGCGT   4560
CGCCGTCGGT   GCATCGTCCG   GCGGCGTTGT   CGTTGCCATC   TCAGAAAATG   ACTCAGTGCT   4620
GTCCGGTTGG   TCGTACCGAT   CCGCACTGTC   AGAGGGCCG    GCGTATGTTT   CGAAGACGTG   4680
GCAGTAGGTA   TCGAAGACCT   GTGAGGAGAG   CACAGTATTG   AGATCGTTGT   GGAGTAAGCC   4740
AGGGCTGCCC   TCCCGGGGCG   GGACAACCGC   AACCCCCATC   TCCTGAGAGA   GGAAGTTGCG   4800
AATCGTCGGG   AGCGTCAACA   CGCTCCACGC   GTCACGAGAC   AGATCGGGCC   CGAGGTCGAG   4860
ATGAACGACG   CTGCCGCGGT   TGTAGCCACC   CGAGAGGATA   CGGTCAAGAT   CACGGATGCC   4920
AGTCGAGAAT   TTCGCCTTCG   AATTTGCCAG   GGATCCCAC    GTGCCATTCC   CGGTTCCTGT   4980
TTGGATGGTT   AGTAATTCGA   CCGGCGTGAT   CACCTGGAAC   TGGCCGTCGG   CAAGCGTAAA   5040
GGGCTGTAAG   CGGTTGCCGA   TTCGAACGCC   CCGAAGCTTA   TCCAAGCGGA   GATCCCGACG   5100
CGTTCGGCCA   CGGTCATCCT   CCTTAACCTG   GAGGGTGACG   ACCCCATCGA   CGATGTATTC   5160
AAGCGATGAG   GGCGCCGCTG   TTTCTGTCAC   TAACATCAGA   CGAATGTTCT   CTTCGCGGGC   5220
AAGAACGGCC   AGTTGATTCG   TCACAGTCTT   GATGTCAGGG   GGGTCATCGT   GGCGAACAGC   5280
CAAATACTCG   TAGATGAGTT   CCCAGCTATC   GAATGCGATT   GTGAGTTGCG   TGGTCGCGGC   5340
GTTGATCTCT   TGGATCCATT   CGAGGAGCGA   ATCCAGATCG   AGTTTCTCGA   ATGGCACGTC   5400
TACGTCCAGT   GGGAGTTCGA   ATGGGTCTTG   GAAGAGGTCA   AGAATCGCGG   TTGTGTCGAG   5460
TGAGGAGTGA   TCGGCGAAGT   ACATCTCGTG   AACCGTCTCC   TGATCAACAC   GTGTGGACAC   5520
GTAGAGGACA   TCACTGTCTC   GGTCCAACAC   ATCGAGGCCG   CGGATCGTGA   ACAAGGTCTT   5580
ACCCGTGCCT   GGTGCACCGT   TAATGAGGAG   CGTTTCCCCG   GCGTCACCCA   TGAAAAACTG   5640
GCTGAGCTCG   CGGGGAATA    ACACGATTCC   GGTGTAGTCT   GTGGGCGGGT   GAGCTAGATT   5700
GGGTGAACTC   ATTACTTCTC   TCCAGTCGAT   GGCGGTAGAG   CACTCCCGAC   TAGTAGGTGA   5760
GGCTTTCTTC   GCTTCACGAC   TGTCTAAGAA   GCTTACACT    CTCCGTACTT   AGAAGTACGA   5820
CTCATTACAG   GAGACATAAC   GACTGGTGAA   ACCATACACA   TCCTTATGTG   ATGCCCGAGT   5880
ATAGTTAGAG   ATGGGTTAAT   CCCAGATCAC   CAATGGCGCA   ACCAGATTCT   TCAGGCTTGG   5940
CAGAAGTCCT   TGATCGTGTA   CTAGACAAAG   GTGTCGTTGT   GGACGTGTGG   GCTCGTGTGT   6000
CGCTTGTCGG   CATCGAAATC   CTGACCGTCG   AGGCGCGGGT   CGTCGCCGCC   TCGGTGGACA   6060
CCTTCCTCCA   CTACGCAGAA   GAAATCGCCA   AGATCGAACA   AGCCGAACTT   ACCGCCGGCG   6120
CCGAGGCGGC   ACCCGAGGCC   TGACGCACAG   GCCTCCCTTC   GGCCGGCGTA   AGGGAGGTGA   6180
ATCGCTTGCA   AACCATACTA   TTAACACCTT   CTCGGGTACA   CACTAATCCC   ATGAGTGTCA   6240
CAGACAAACG   CGACGAGATG   AGTACTGCCC   GCGATAAGTT   CGCAGAATCA   CAGCAGGAGT   6300
TCGAATCATA   CGCTGACGAG   TTTGCAGCCG   ATATCACGGC   AAAGCAAGAC   GATGTCAGCG   6360
ACCTTGTCGA   TGCGATCACC   GACTTCCAGG   CGGAGATGAC   CAACACGACG   GATGCATTTC   6420
ACACATATGG   TGACGAGTTC   GCCGCTGAGG   TTGACCACCT   CCGTGCCGAT   ATTGACGCCC   6480
AGCGGGACGT   GATCCGTGAG   ATGCAGGATG   CGTTCGAGGC   ATATGCTGAC   ATCTTCGCTA   6540
CAGATATCGC   AGACAAACAA   GATATCGGCA   ATCTTCTGGC   TGCGATTGAG   GCGCTCCGAA   6600
```

-continued

```
CAGAGATGAA CTCAACCCAC GGGGCATTCG AAGCATATGC GGACGACTTC GCAGCCGATG    6660
TCGCTGCGCT CCGTGATATA TCTGATCTGG TTGCAGCAAT CGACGACTTC CAAGAGGAAT    6720
TCATCGCCGT GCAGGACGCA TTTGACAACT ACGCTGGTGA CTTCGATGCG GAGATCGACC    6780
AGCTCCACGC TGCCATCGCT GACCAGCACG ACAGCTTCGA CGCTACCGCG GACGCCTTCG    6840
CAGAGTACCG AGATGAGTTC TATCGCATAG AGGTGGAAGC ACTGCTTGAG GCGATCAACG    6900
ACTTCCAGCA GGACATCGGT GACTTCCGAG CGGAGTTTGA AACGACTGAG GACGCGTTCG    6960
TTGCCTTCGC CCGTGACTTC TATGGCCACG AGATCACGGC CGAGGAAGGC GCCGCCGAAG    7020
CGGAAGCCGA ACCCGTCGAG GCTGACGCGG ACGTCGAAGC GGAAGCAGAA GTCTCTCCAG    7080
ACGAAGCTGG CGGAGAATCC GCCGGTACCG AGGAAGAAGA GACAGAGCCG GCCGAGGTGG    7140
AAACAGCGGC TCCAGAAGTA GAGGGGAGTC CTGCGGACAC GGCAGACGAA GCGGAAGATA    7200
CGGAAGCAGA GGAGGAGACA GAGGAAGAGG CACCGGAAGA CATGGTGCAG TGCCGGGTGT    7260
GCGGCGAATA CTATCAGGCC ATCACGGAGC CCATCTCCA GACCCATGAT ATGACGATTC    7320
AGGAGTACCG CGACGAGTAC GGTGAGGATG TCCCCCTTCG GCCGGATGAT AAAACATGAC    7380
GAACGAGTCC CGTAAACGCA AGGTACGAGG GTCGCAGATC CGCTCCTCAC GCGGCGACAA    7440
GAAACAGGGG CGATCACAGA GCCGTGATGA TAAGGAGATC GAGCGTCTCG AGAGGCAGAA    7500
CGACGCTCGT GGCCAGGAGT CGTCTACCCA CGTCGACGAG GGGTTCGTTC CGAGGAACA    7560
GTCCTTCATC GAGACCGAAT CGGTCAATCG AGTCGAGTCG CGGATGGAAC GGTGGCTCGA    7620
TGTCGGACGT CCGGTTCACC TGATCGGGCC GACCGGCTGT GGGAAAACGT CGCTGGCGAT    7680
GCACGTCGCG CGCGAGCGCG ATCGCCCGGT CGTCTGGATC AACGGCGACG CCGAACTCAC    7740
GACCAGCGAT CTCGTCGGCG AATACGCGGA AAAAGAGCGC ATCTCGGAGC ACGATCAATT    7800
CATCCACAAC GTCGTTAAGA GCAAGGACAT CATCCGTGAT CGATGGGTGG ACAACCCCCT    7860
GACGCTCGCC GTACAAGAGG GGGCAACGCT GGTCTACAAC GAGTTCTCCC GCACCAAGCC    7920
CGTCGCAAAC AACGTGCTGT TGTCGGTCTT CGAGGAAGGG GTGCTCGAAC TGCCGGGGAA    7980
ACGCGGCAAA TCTCGGTATG TAGATGTGCA TCCTGAGTTC CGAACCATCC TGACCTCGAA    8040
CTCCGTCGAG TACGCTGGCG TCCACGAGCC GCAAGACGCC CTGCTCGACC GCCTCATCGG    8100
GATCTACATG GATTTCTACG ATCTCGACAC GGAGATCGAG ATCGTTCGGG CGCACGTCGA    8160
CAAGTCGGCC GACACAAACG TCGAGGACAT CGTGCGGGTT CTGCGTGAAC TCCGCGAGCG    8220
GCTCGATATC ACCGTGGGTA CACGGGCCGC GATTATGGCC AACGAAGGCG CTACCACCGT    8280
CGACACCGTC GACCAGGCCG TCCTGACCGA TATCTGTACC GACGTGCTGG CATCGAAGGT    8340
CGCCCAGCGG AGCGACGTTC GCGGGCTGCG CGAAGAAATA GAATCCGCGA TCGACGACAT    8400
GGAAGTCGCC CTTTCTTAAG ATCCGGGGTC TCTACATAGA AGCATGGCAG ATCCAGCAAA    8460
CGATCGATCT GAACGCGAGG AAGGCGGCGA GGACGACGAA ACACCGCCAG CGTCCGACGG    8520
GAACCCCTCG CCGTCGGCCA ATTCATTCAC TCTCTCCAAC GCGCAGACGC GCGCACGAGA    8580
GGCGGCACAG GACCTGTTGG AACACCAGTT CGAGGGATGA TCAAAGCCGA GTCGAACGAC    8640
GAAGGCTGGC GGACCGTCGT CGAAGTCGTC GAACGGAACG CCGTACCCGA TACACAAGAC    8700
ATCATCGGTC GCTACGAGAT CACGCTTGAC GGGACGGGGG ACGTCACCGG CTACGAGCTC    8760
CTAGAACGCT ATCGTCGGGG CGACATGAAA GAGGAACTGT AGCGGTGCGT CAAATGCACG    8820
AGCAATAGAT ATGGCCCATC GACTGACCGT AGCGAACGAG AAAGGCGGCG TGGGGAAG     8878
```

( 2 ) INFORMATION FOR SEQ ID NO:3:

( i ) SEQUENCE CHARACTERISTICS:

(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:3:

Glu Ala Asp Ala Asp Val Glu Ala Glu Ala Glu
1               5                   10

RECOMBINANT GAS VESICLES AND USES THEREOF

CROSS REFERENCE TO RELATED APPLICATION

This application claims the benefit of provisional application Ser. No. 60/008,200, filed Dec. 5, 1995.

BACKGROUND OF THE INVENTION

The invention relates to recombinant gas vesicles and uses thereof.

Traditional vaccines consist of killed or attenuated pathogens or their isolated toxins and normally include a variety of epitopes. However, it has long been known that portions of molecules can be recognized by the immune system and that antibodies developed against the appropriate epitope(s) can result in protective immunity. As a result, there has been considerable interest in developing vaccines composed of less than the entire pathogen. Subunit vaccines, which include all or a part of a protein subunit of the infectious organism, and peptide vaccines are examples of such vaccines. The immunogens of subunit and peptide vaccines are typically not sufficiently immunogenic unless they are administered in conjunction with an adjuvant, or are cross-linked to a large molecular weight protein such as keyhole limpet hemocyanin (KLH).

The desire to use vaccines which do not involve administration of killed or attenuated pathogens has led to the development of specialized vaccine systems. Among these newer systems are conjugate/carrier systems that are designed to improve the immunogenicity and delivery of smaller antigens by physically associating, often by chemical means, separately produced epitope and carrier/adjuvant components. Recombinant systems in which the immunogen is produced as a part of a larger chimeric molecule represent a second approach to improving immunogenicity and delivery of immunogens. Direct delivery of DNA represents another non-traditional vaccine system.

Liposomes and microbeads have been suggested as conjugate/carrier systems. Because liposomes have the ability to fuse with biological membranes, they have been tested in the peroral delivery of a variety of other immunogens (Rouse, *J. Am. Vet. Med. Assoc.* 181:988–991, 1982; Childers et al., *Regional Immunol.* 3:289–296, 1991). As an alternative, antigens have been incorporated into synthetic, degradable microbeads which are thought to stimulate the immune system and deliver molecules as particulate entities. This delivery system can be adapted to contain incorporated adjuvant and/or cytokines. Moreover, microbeads can be designed to provide a sequential release of antigen through timed biodegradation of the particle. (O'Hagan et al., *Vaccine* 9:768, 1991; O'Hagan et al., *Immunology* 73:239, 1991). In addition, bacterial S-layers also have been studied as conjugate/carrier vehicles. Because their natural repeat spacing provides a defined geometric matrix, the chemical crosslinking of immunogen(s) to this carrier results in the display of epitopes at known intervals and defined densities (Herzenberg et al., *J. Exp. Med.* 155:1730, 1982; Schneersson et al., *Infect. & Immun.* 52:519, 1986; Schultze et al., *J. Immunol.,* 135:2319, 1987; Schultze et al., *J. Immunol.,* 135:2319, 1987; Russell et al., *Infect. & Immun.* 59:4061, 1991).

Recombinant vaccines represent a second type of non-traditional of vaccine system. Recombinant vaccines involve genetically engineering the immunogen and its associated carrier, which can be an attenuated pathogen, as a single chimeric unit. Using this broad approach, viral capsid and recombinant bacteriophage have been engineered to display peptides on their surface (Notkins et al., *Science* 228:737, 1985; Smith, *Science* 228:1315, 1985; Clarke et al., *Nature* 330:381, 1987; Dedieu et al., *J. Virol.* 66:3161, 1992). Some recombinant vaccines use live, attenuated bacteria to deliver an exogenous antigen (Schodel et al., *Infect. Immun.* 62:1669, 1994; Fairweather et al., *Infect. & Immunol.* 58:1323, 1990; Sutter et al., *Proc. Nat'l Acad. Sci.*89:10847, 1992; Scheiflinger et al. *J. Bacteriol.* 174:595, 1992; Andino et al., *Science* 265:1448, 1995).

Recombinant vaccines may be able to serve as multivalent antigen delivery vehicles capable of repeated use. However, there may be significant drawbacks associated with the use of these recombinant vaccines. First, it is possible that subsequent exposure of vaccinated hosts to such carriers could result in severe immunological reactions because of sensitization to the carrier. Second, where attenuated pathogens are used, genetic recombination may pose a long term threat of reactivating the attenuated strain. Finally, the expense of cell culture and the need for large quantities viable recombinants, may make large scale vaccination programs prohibitively expensive.

DNA-mediated immunization represents a third approach non-traditional approach to vaccination. In this approach, DNA encoding the relevant antigen is introduced directly or indirectly into the individual being immunized. For example, the relevant DNA sequences can be inserted into a plasmid which is carried by bacteria. The plasmid DNA is taken up by the eukaryotic cells and this host's biosynthetic machinery then is co-opted to produce the encoded protein (s) (see, e.g., Ulmer et al., *Science* 259:1745, 1993; Sizemore et al., *Science* 270:299–302, 1995). Barry et al. (*Nature* 377:632–635, 1995) discloses a different approach to genetic immunization referred to as "expression-library immunization." In expression-library immunization an expression library of multiple DNA sequences defining a particular pathogen is prepared and used via genetic immunization to stimulate a protective immune response. This approach, in theory, permits exposure of a host to an array of pathogen antigens without the concomitant risks normally associated with the use of the pathogen itself. As with any use of DNA per se, its potential integration into the host genome and disruption of normal gene function must be considered.

SUMMARY OF THE INVENTION

The invention features a composition that includes substantially pure recombinant gas vesicles which have at least one heterologous peptide inserted into at least one gas vesicle structural protein. The recombinant gas vesicles, when administered to a mammal, are capable of eliciting antibodies which specifically bind to the heterologous peptide. The heterologous peptide can be any peptide against which one wishes to raise antibodies, e.g., a peptide found in the gp120 protein of human immunodeficiency virus (HIV). Preferably the gas vesicle structural protein is a gvpA-related or gvpc-related protein.

By "peptide derived from" a particular organism or protein is meant a peptide having a sequence that is the same as all or part of a protein found in that organism or protein.

By "gvpA-related protein" is meant a protein which is both homologous to and functionally equivalent to the gvpA protein of *Halobacterium halobium*. By "gvpC-related protein" is meant a protein which is both homologous to and functionally equivalent to the gvpc protein of *Halobacte-*

*rium halobium.* Preferred proteins for insertion of peptides are the gvpA or the gvpc protein of *Halobacterium halobium.* Preferred gas vesicles are the gas vesicles of *Halobacterium halobium.*

The heterologous peptide is inserted, in frame, into the gas vesicle structural protein by preparing a chimeric gene. Those skilled in the art can prepare a nucleic acid molecule encoding the peptide of interest. This nucleic acid molecule can be inserted into a gene encoding a gas vesicle structural protein to prepare a recombinant gas vesicle gene which encodes gas vesicle protein with the peptide inserted in frame. The sequence of the peptide can be based on the sequence of all or part of any desired protein present in the molecule or pathogen or organism to which antibodies are to be raised.

By "peptide" is meant any chain of amino acids, regardless of length or post-translational modification, e.g., glycosylation or phosphorylation, and includes polypeptides and proteins. Preferred peptides for insertion into gas vesicle proteins are at least 50 amino acids long, more preferably at least 20 amino acids long, even more preferably at least 10 amino acids long. They may also be at least 7, 6, or 5 amino acids long or even at least. Peptides can also be 5 kD or even larger.

By "substantially pure" is meant a preparation, e.g., of recombinant gas vesicles, which is at least 60% by weight (dry weight) the material of interest, e.g., recombinant gas vesicle. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis. Amino acid analysis is the preferred method for assessing the purity of gas vesicles.

An antibody that "specifically binds" as peptide is an antibody that recognizes and binds the selected peptide but which does not substantially recognize and bind other molecules in a sample, e.g., a biological sample, which naturally includes the selected peptide. Specific e binding can be measured using an ELISA assay in which the selected peptide is used as an antigen.

By "structural protein" is meant a protein present in mature complete gas vesicles. By "surface protein" is meant a protein present on the external surface of mature complete gas vesicles.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1, panel B is a graph depicting the results of ELISA used to measure the level of particular antibodies present in the serum of mice 2 weeks after a first immunization with WT-TNP GV. In this set of experiments BSA-TNP was used as the antigen for ELISA.

FIG. 1, panel C is a graph depicting the results of ELISA used to measure the level of particular antibodies present in the serum of mice after a second immunization with WT-TNP GV. In this set of experiments BSA-TNP was used as the antigen for ELISA.

FIG. 1, panel D is a graph depicting the results of ELISA used to measure the level of particular antibodies present in the serum of mice after a second immunization with WT-TNP GV. In this set of experiments BSA-TNP was used as the antigen for ELISA.

In FIG. 1, panels A–D the following symbols were used: filled circles: 1 mg WT-TNP GV IgM; filled triangles: 0.1 mg WT-TNP GV IgM; filled diamonds: 1 mg WT GV IgM; open circles: 1 mg WT-TNP GV IgG; open triangles: 0.1 mg WT-TNP GV IgG; open triangles: 0.1 mg WT-TNP GV IgG; open diamonds: 1 mg WT GV IgG; and open squares: buffer IgG.

FIG. 2, panel A is a graph depicting the results of ELISA used to measure the level of particular antibodies present in the serum of mice 4 weeks after immunization with mutant-TNP GV. In this set of experiments BSA-TNP was used as an antigen for ELISA.

FIG. 2, panel B is a graph depicting the results of ELISA used to measure the level of particular antibodies present in the serum of mice 4 weeks after immunization with mutant-TNP GV. In this set of experiments BSA-TNP was used as an antigen for ELISA.

FIG. 2, panel C is a graph depicting the results of ELISA used to measure the level of particular antibodies present in the serum of mice after a second immunization with mutant-TNP GV. In this set of experiments BSA-TNP was used as an antigen for ELISA.

FIG. 2, panel D is a graph depicting the results of ELISA used to measure the level of particular antibodies present in the serum of mice after a second immunization with mutant-TNP GV. In this set of experiments BSA-TNP was used as an antigen for ELISA.

In FIG. 2, panels A–D, the following symbols were used: filled circles: mutant-TNP GV IgM; filled squares: buffer IgM; open circles: mutant-TNP GV; and open squares: buffer.

FIG. 3, panel B is a graph depicting the results of ELISA used to measure the level of particular antibodies present in the serum of mice after a second immunization with mutant-TNP GV. In this set of experiments the 7 amino acid peptide (ESSGTFE) (SEQ ID NO:1) present in mutant GV was used as an antigen for ELISA.

In FIG. 3, panels A and B, the following symbols were used: filled circles: mutant-TNP GV IgM; filled squares: buffer IgM; open circles: mutant-TNP GV; and open squares: buffer.

FIG. 4, panel A is a graph depicting the results of ELISA used to measure the level of particular antibodies present in the serum of mice 10d after a reinoculation 8 months after the original immunization.

FIG. 5, panel B is a graph depicting the results of ELISA used to measure the level of particular antibodies present in the serum of mice 17d and 39d after a reinoculation 8 months after the original immunization.

FIG. 6 is the nucleotide sequence of the gvp gene cluster of *Halobacterium halobium* (SEQ ID NO:2).

DETAILED DESCRIPTION

Figure 1A:
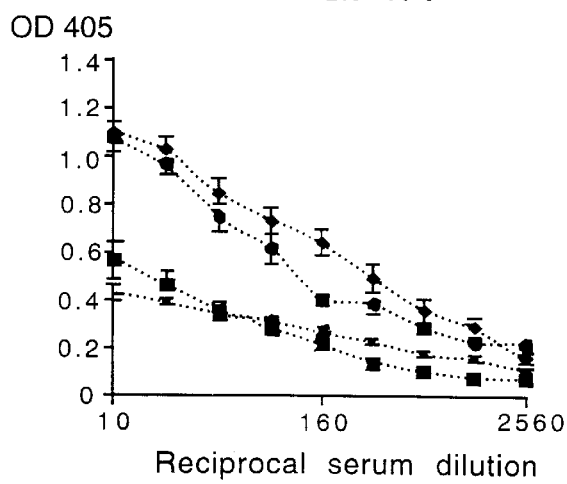
FIG. 1, panel A is a graph depicting the results of ELISA used to measure the level of particular antibodies present in the serum of mice 2 weeks after a first immunization with WT-TNP GV. In this set of experiments BSA-TNP was used as the antigen for ELISA.
Figure 1B:
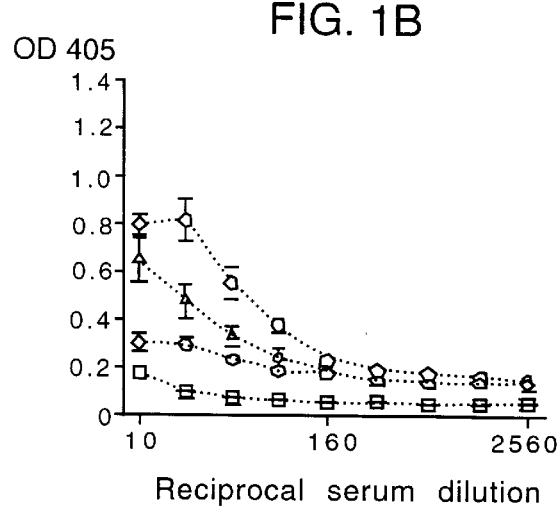
Figure 1C:
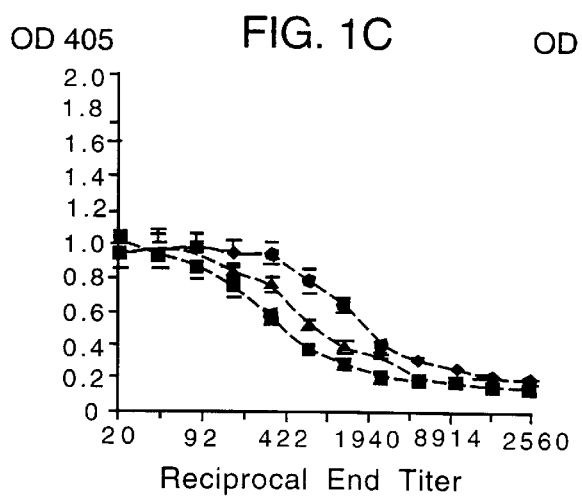
Figure 1D:
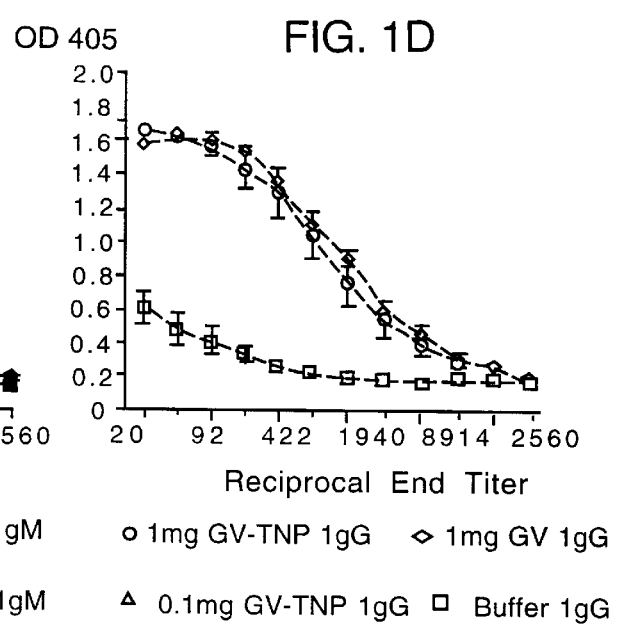

Described below are methods which can be used to prepare recombinant gas vesicles having a heterologous peptide inserted into protein component of the vesicle.

Preparation of recombinant vesicles for use in eliciting antibodies includes four basic steps: (1) insertion of DNA encoding the peptide of interest into a coding sequence of a halobacterium gas vesicle protein to create a chimeric gas vesicle protein; (2) transformation of halobacterium or some other suitable bacteria capable of producing gas vesicles with the DNA encoding the chimeric protein; (3) growing the bacteria under conditions which permit the expression of the chimeric protein and formation of gas vesicles; and (4) and harvesting and purifying the gas vesicles.

U.S. patent application Ser. No. 08/271,270 (Recombinant Vector and Process for Cell Floatation), now abandoned, includes useful methods related to gas vesicles and is incorporated by reference.

Introduction of Heterologous Peptides

Any selected peptide, e.g., a peptide of a pathogen, can be introduced into a gas vesicle protein to produce recombinant gas vesicles capable of eliciting an immune response to the selected peptide when the vesicle is introduced into a mammal. Recombinant gas vesicles can bear a peptide normally found in HIV, *Plasmodium falciparum, Salmonella typhi*, mycoplasm, or any other pathogenic organism. In some cases it may be desirable to introduce two or more heterologous peptides into a single recombinant gas vesicle. The several peptides can be derived from the same or different pathogenic organisms and can be inserted into the same gas vesicle protein or into different gas vesicle proteins.

The recombinant gas vesicles of the invention can be used to present a wide variety of antigens. Among the suitable peptides are peptides derived from the coat protein of HIV, particularly the principal neutralizing domain of HIV (Dedieu et al., *J. Virol.* 66:3161, 1992); peptides derived from herpes simplex virus type 1 glycoprotein D (Notkins et al., *Science* 228:737, 1985); and peptides derived from hepatitis B virus core-pre-s protein (Schodel et al., Infect. Immun. 62:1669, 1994). Other useful peptides can be derived from peptide toxins produced by pathogens. Generally, many of the peptides presented by genetically engineered vaccines can be used. A detailed description of peptides used in genetically engineered vaccines can be found in Ciardi et al., "Genetically Engineered Vaccines" (Plenum Press, New York, 1992).

The selected heterologous peptide can be inserted into a gas vesicle structural protein at any suitable location. The peptide may also be place at the carboxy terminus of the protein, e.g., at the carboxy terminus of gvpc or gvpA. Preferred locations for insertion are within the repeats of the gvpc protein or a gvpC-related protein.

Under some circumstances it may be desirable to insert two or more peptides into a particular structural protein. The presence of multiple antigens can often elicit a stronger or more protective immune response. When two or more peptides are inserted into a single gas vesicle structural protein, they can be derived from the same or different pathogenic organism. When multiple peptides are inserted they can be inserted at different locations within the gas vesicle structurallprotein or adjacent to each other at the same location. It is not necessary that the peptides be different. Thus, one can insert multiple copies of the same peptide into a gas vesicle structural protein.

The recombinant gas vesicles can be used to create compositions suitable for expression library immunization. In this technique a library of peptide-encoding random DNA fragments is prepared and inserted into one or more selected locations in a DNA molecule encoding a gas vesicle structural protein, e.g., a plasmid bearing the gvpMLKJIHGFE-DACN gene cluster of *Halobacterium halobium*. This process results in the creation of a population of DNA molecules which can be used to transform bacteria. The resulting clones can be used for the production of recombinant gas vesicles. By purifying gas vesicles from a mixture of gas vesicle-producing clones, it is possible to create a "cocktail" of recombinant gas vesicles which can be injected into a patient in order to elicit an immune response.

A preferred site for insertion of peptides is between the V and E of the following gvpC sequence of *Halobacterium halobium*: EADADV[INSERTION SITE]EAEAE (SEQ ID NO:3).

Preparation and Isolation of Recombinant Gas Vesicles

Simon et al. (*Archaea—A Laboratory Manual—Halophiles*, DasSarma et al., eds., Cold Spring Harbor Laboratory Press, 1995) describes useful techniques for working with halophilic bacteria.

The preferred means of inducing a bacterial cell to produce gas vesicles is to transform the cell with a plasmid bearing the gvpMLKJIHGFEDACN gene cluster of *Halobacterium halobium*. The plasmids pNRC100, pJHGV3, and pFL2 (DasSarma et al., *J. Bact.* 176:7646, 1994) is a suitable plasmid bearing genes required for expression of gas vesicles. The plasmids pJHGV3 and pFL2 are *H. halobium-Eschericia coli* shuttle plasmids that are particularly useful for the preparation of recombinant gas vesicles.

It is preferable that the heterologous plasmid be inserted into the GvpA gene or the GvpC gene which have been identified in *Haloferax mediterranei* (Englert et al., *J. Biol. Chem.* 268:9329, 1993), *Halobacterium halobium* (Halladay et al., *J. Bateriol.* 175:684, 1993), and other bacteria (Walsby et al., *J.Gen. Microbiol.*, 134:2647, 1990). Walsby (*Microbiol. Rev.* 58:94, 1994) describes bacteria that express gas vesicles. Under some circumstances it is desirable to engineer suitable restriction sites into GvpA, GvpC, or other gas vesicle proteins. Suitable insertion sites, e.g., restriction sites, can be generated by site-directed mutagenesis. *Current Protocols in Molecular Biology*, (John Wiley & Sons, New York, 1994) describes the use of site-directed mutagenesis, as well as a wide variety of other techniques that can be used to construct recombinant gas vesicles useful in the invention.

*H. halobium* can be cultured in a medium containing 4.3M NaCl as described by DasSarma et al. (*Proc. Nat'l Acad. Sci. USA* 85:6861, 1988). The nucleotide sequence of the gvp gene cluster of *H.halobium* is disclosed in Halladay (*J. Bact.* 175:684, 1993). A partial sequence is disclosed in Jones et al. (*Gene* 102:117, 1991). FIG. 6 includes a sequence of the gvp gene cluster of *H. halobium*.

*H. halobium* can be transformed using the EDTA-polyethylene glycol procedure of Cline et al. (*J. Bateriol.* 169:1341, 1987).

Recombinant Gas Vesicles Can Elicit a Long-Lived Immune Response

Wild type (WT) and peptide-inserted gas vesicles (GV) were prepared as follows. *Halobacterium halobium* SD109 (pFL2) (WT GV) and SD109(pFL2C::K1Δ) (Modified GV; includes the peptide ESSGTF insert into gvpc of *Halobacterium halobium* at between the V and E of the sequence EADADVEAEAE) (SEQ ID NO:3) were grown to confluency on peptone-salt plates supplemented with 10 $\mu$M B mevinoloin. Gas vesicles were isolated by centrifugally accelerated floatation (Simon et al., supra). The yield of gas vesicles was approximately 10 mg/l of plates (plate surface area/liter was approximately 1134 $cm^2$).

A portion of the WT and peptide inserted GV were used to prepare trinitrophenol (TNP)-modified WT and peptide inserted GV as follows. Modification used was performed according to the modification procedure described by Little et al. (Methods in Immunology and Immunochemistry, Vol. 1, pp. 128–133, 1967). Briefly, approximately 10 mg of each type of GV was incubated with 2,4,6 trinitrobenzene sulfonic acid over night at room temperature in the dark. The GV were then purified by dialysis against PBS (150 mM NaCl; 10 mM phosphate, pH 7.5).

Groups of 8 week old mice (4 per group) were injected intraperitoneally (approximately 0.5 mg/GV per animal) with WT, mutant, WT-TNP, or mutant-TNP gas vesicles. A group of mice were injected with PBS as a control. Serum was collected 2 weeks and 4 weeks after the primary immunization. The mice were then boosted with an additional 0.5 mg of GV. Serum was collected again 10 days after the secondary immunization. The injections did not have a significant effect on weight gain. No lesions were observed at the site of injection.

Immune response was measured by ELISA using either bovine serum albumin conjugated to TNP (BSA-TNP) or the seven amino acid peptide present in mutant GV as antigen. Anti-mouse IgG horseradish peroxidase or anti-mouse IgM horseradish peroxidase. The results of this analysis are presented in FIGS. 1–3.

FIG. 1 depicts the results of experiments in which WT-TNP GV were used to immunize mice and BSA-TNP was used as an antigen for ELISA. FIG. 1, panels A and B present the results for the 2 week primary IgM response and the 2 week primary IgG response respectively while panels C and D present the secondary IgM and IgG response (filled circles: 1 mg WT-TNP GV IgM; filled triangles: 0.1 mg WT-TNP GV IgM; filled diamonds: 1 mg WT GV IgM; open circles: 1 mg WT-TNP GV IgG; open triangles: 0.1 mg WT-TNP GV IgG; open triangles: 0.1 mg WT-TNP GV IgG; open diamonds: 1 mg WT GV IgG; open squares: buffer IgG).

FIG. 2 depicts the results of experiments in which mutant-TNP GV were used to immunize mice and BSA-TNP was used as an antigen for ELISA. FIG. 2, panels A and B present the results for the 4 week primary IgM response and the 4 week primary IgG response respectively while panels C and D present the secondary IgM and IgG response (filled circles: mutant-TNP GV IgM; filled squares: buffer IgM; open circles: mutant-TNP GV; open squares: buffer).

Figure 3A:
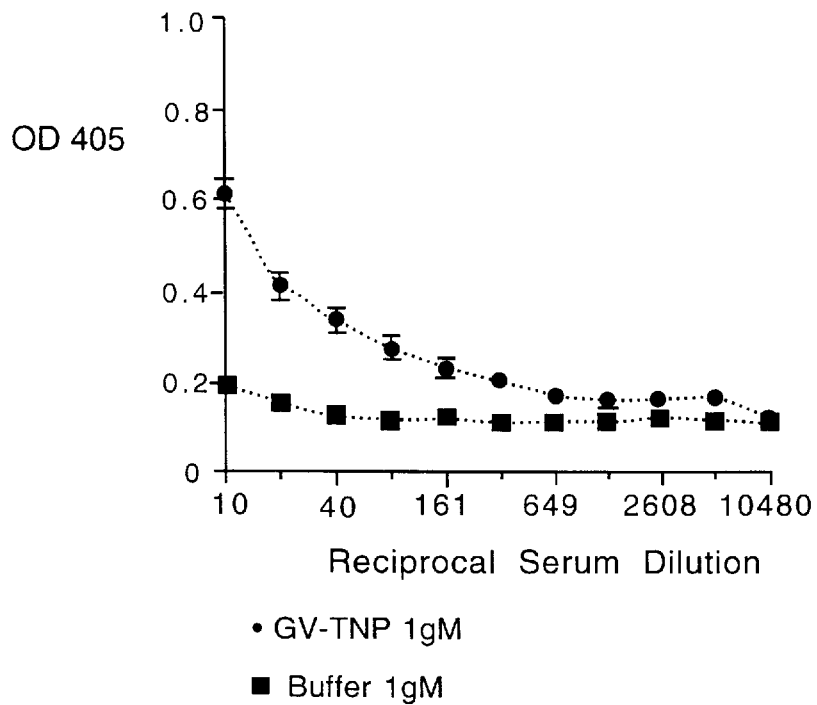
FIG. 3, panel A is a graph depicting the results of ELISA used to measure the level of particular antibodies present in the serum of mice after a second immunization with mutant-TNP GV. In this set of experiments the 7 amino acid peptide (ESSGTFE) (SEQ ID NO:1) present in mutant GV was used as an antigen for ELISA.
Figure 3B:
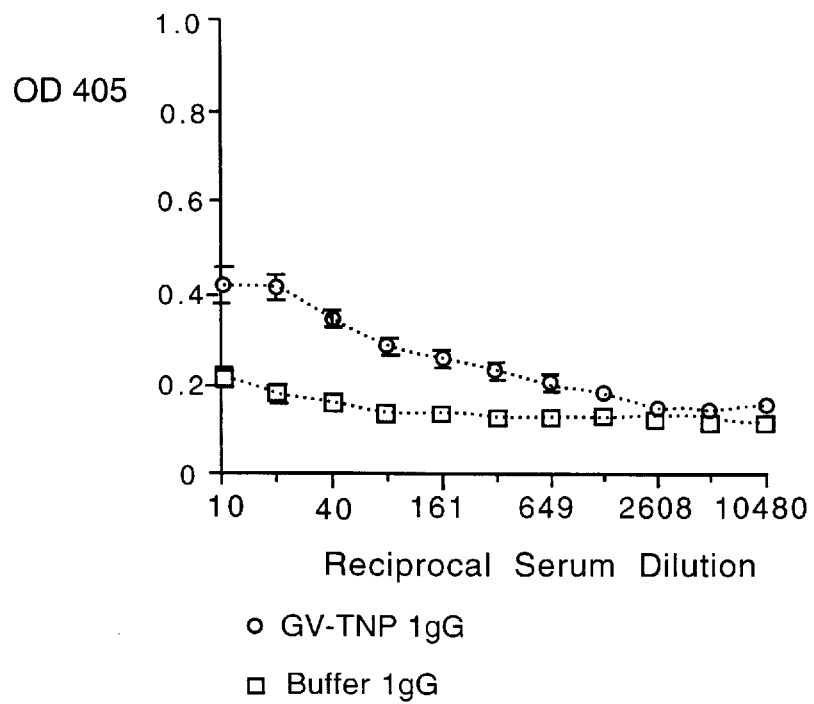
Figure 4A:
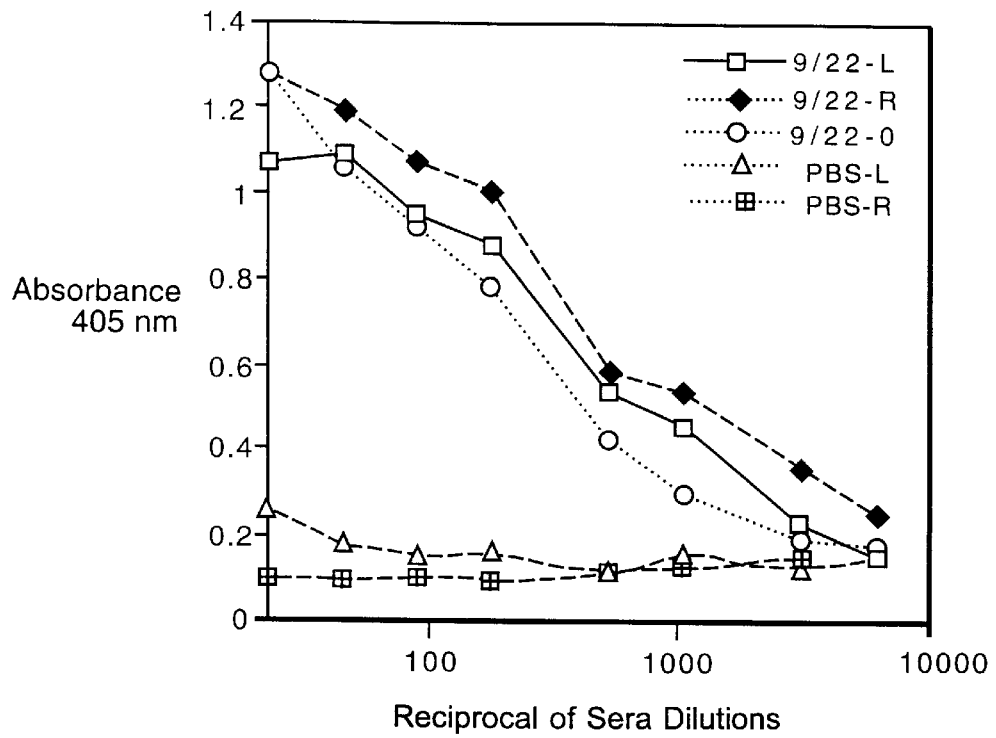
FIG. 4, panel B is a graph depicting the results of ELISA used to measure the level of particular antibodies present in the serum of mice 7d after a reinoculation 8 months after the original immunization.
Figure 4B:
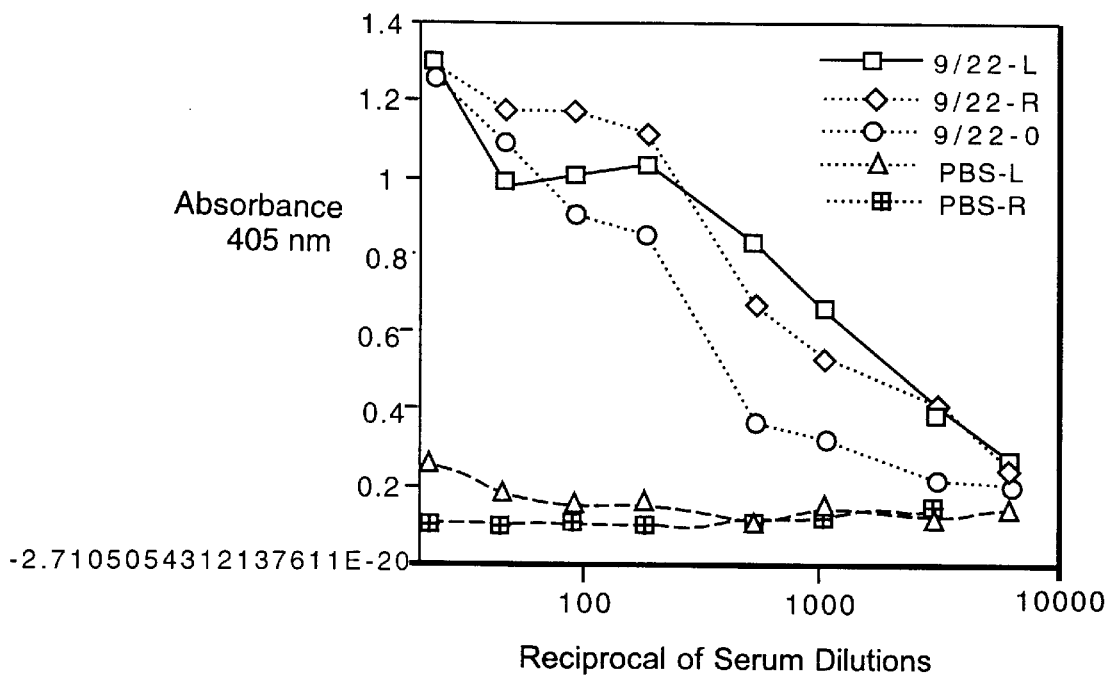

FIG. 3 depicts the results of experiments in mutant-TNP GV were used to immunize mice and the 7 amino acid peptide (ESSGTFE) (SEQ ID NO:1) present in mutant GV was used as an antigen for ELISA. FIG. 3, panels A and B present the results for secondary IgM and secondary IgG response (filled circles: mutant-TNP GV IgM; filled squares: buffer IgM; open circles: mutant-TNP GV IgG; open squares: buffer IgG).

These results demonstrate that GV can effectively present TNP and peptide haptens in the absence of added adjuvant. These experiments also demonstrate that both IgG and IgM responses can be elicited. The IgG response increased after the secondary immunization while the IgM response peaked prior to the boost.

Figure 5A:
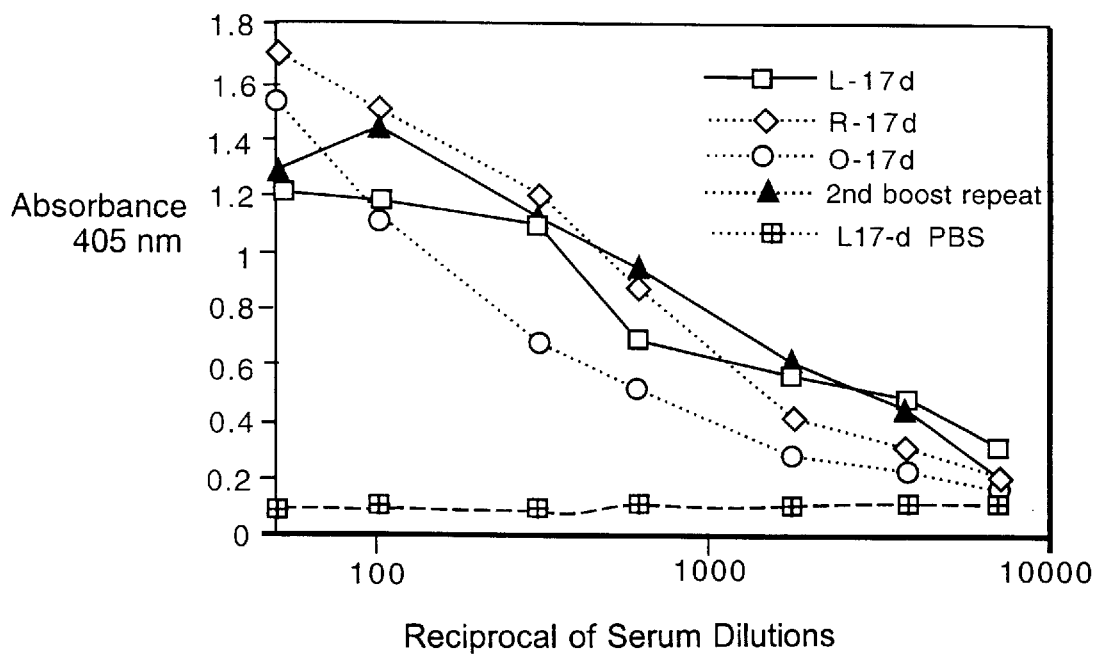
FIG. 5, panel A is a graph depicting the results of ELISA used to measure the level of particular antibodies present in the serum of mice 17d after a reinoculation 8 months after the original immunization.
Figure 5B:
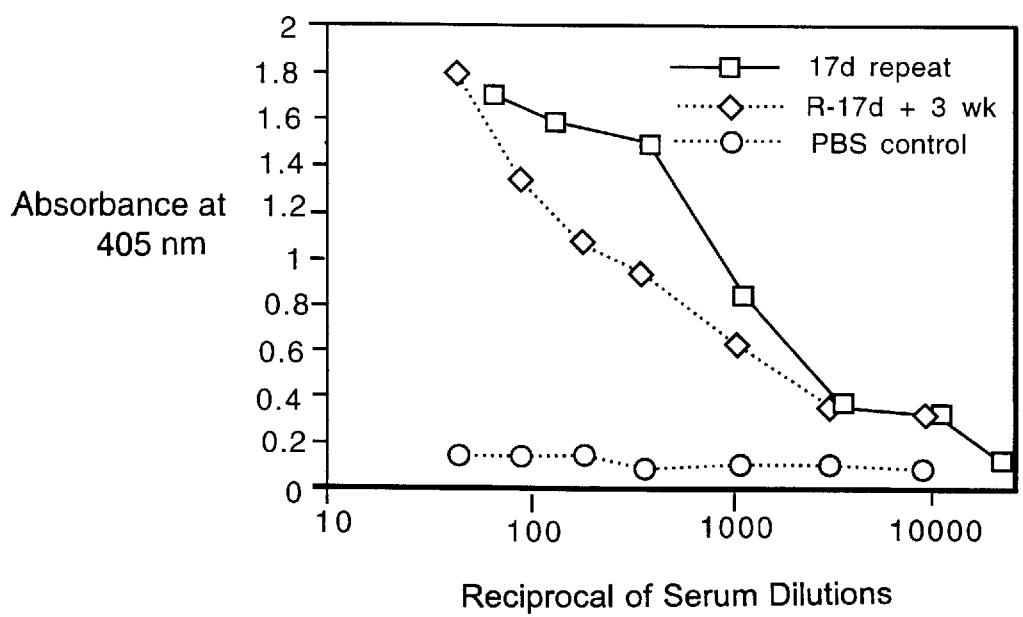

FIG. 5, panel A, FIG. 5, panel B, FIG. 6, panel A, and FIG. 6, panel B present the results of ELISA used to demonstrate the immune response elicited by the gas vesicles lasts for months.

These results demonstrate that gas vesicles having a peptide inserted into a gas vesicle structural protein can elicit a long-lived immune response. Accordingly, such gas vesicles can be used as a vaccine.

Use

The recombinant gas vesicles of the invention may be used to immunize patients using standard methods. Generally they are mixed with a pharmaceutically acceptable carrier and administered by injection.

Animal models, e.g., the murine model described herein, can be used to test the immune response elicited by a selected recombinant gas vesicle. Animal models can also be used by those skilled in the art to estimate the dosage required to provide protection against a given pathogen. In general, methods and dosages for recombinant vaccines used by those skilled in the art are applicable to the vaccines of the present invention.

We claim:

1. A composition comprising substantially pure recombinant gas vesicles comprising a selected peptide inserted in-frame into a structural protein of said recombinant gas vesicle, said composition, when injected into a mammal, elicits antibodies which specifically bind said selected peptide.

2. The composition of claim 1 wherein said peptide is derived from a pathogen.

3. The composition of claim 5 wherein said viral coat protein is gp120.

4. The composition of claim 1 wherein said gas vesicle is a *Halobacterium halobium* gas vesicle.

5. The composition of claim 2 wherein said peptide is derived from a viral coat protein.

6. The composition of claim 4 wherein said peptide is inserted into the gvpC protein.

7. The composition of claim 4 wherein said peptide is inserted into the gvpA protein.

8. A method for eliciting, in a non-human mammal, antibodies which specifically bind a selected peptide, said method comprising:

injecting into said mammal substantially pure recombinant gas vesicles comprising a selected peptide inserted in-frame into a surface protein of said recombinant gas vesicle, wherein said mammal produces antibodies which specifically bind said selected peptide.

9. The method of claim 8 wherein said recombinant gas vesicles comprise distinct recombinant gas vesicles each comprising a different selected peptide.

10. The method of claim 8 wherein said gas vesicles comprise at least two selected peptides.

* * * * *

UNITED STATES PATENT AND TRADEMARK OFFICE
CERTIFICATE OF CORRECTION

PATENT NO.  : 5,824,309
DATED       : October 20, 1998
INVENTOR(S) : Shiladitya DasSarma, Fazeela Morshed, Elizabeth Stuart and Samuel Black It is certified that error appears in the above-identified patent and that said Letters Patent is hereby corrected as shown below:

In column 1, before "CROSS REFERENCE TO RELATED APPLICATIONS" insert the following paragraph:

--This invention was made with government support under grant #MCB-9221144 by the National Science Foundation, and the government has certain rights to the invention.--

Signed and Sealed this

Twenty-fifth Day of May, 1999

Attest:

Q. TODD DICKINSON

*Attesting Officer*    *Acting Commissioner of Patents and Trademarks*